United States Patent
Hassinen et al.

(10) Patent No.: US 11,547,668 B2
(45) Date of Patent: Jan. 10, 2023

(54) VIRAL VECTOR STABILIZATION

(71) Applicant: Trizell Ltd., Chinnor (GB)

(72) Inventors: Minna Hassinen, Kuopio (FI); Robert Shaw, Chinnor (GB); Nigel Parker, Chinnor (GB)

(73) Assignee: Trizell Ltd., West Drayton (GB)

( * ) Notice: Subject to any disclaimer, the term of this patent is extended or adjusted under 35 U.S.C. 154(b) by 0 days.

(21) Appl. No.: 16/931,600

(22) Filed: Jul. 17, 2020

(65) Prior Publication Data

US 2020/0352861 A1   Nov. 12, 2020

Related U.S. Application Data

(62) Division of application No. 15/781,707, filed as application No. PCT/US2017/025727 on Apr. 3, 2017, now Pat. No. 11,311,487.

(60) Provisional application No. 62/322,452, filed on Apr. 14, 2016.

(51) Int. Cl.
| | |
|---|---|
| *C12N 7/00* | (2006.01) |
| *A61K 9/19* | (2006.01) |
| *A61K 47/42* | (2017.01) |
| *C12N 15/86* | (2006.01) |

(52) U.S. Cl.
CPC ........... *A61K 9/19* (2013.01); *A61K 47/42* (2013.01); *C12N 7/00* (2013.01); *C12N 15/86* (2013.01); *C12N 2710/10343* (2013.01)

(58) Field of Classification Search
None
See application file for complete search history.

(56) References Cited

U.S. PATENT DOCUMENTS

| | | |
|---|---|---|
| 8,043,612 B2 | 10/2011 | Roberts et al. |
| 11,311,487 B2 | 4/2022 | Hassinen et al. |
| 2003/0170216 A1 | 9/2003 | Ihnat et al. |
| 2005/0025742 A1 | 2/2005 | Engler |
| 2008/0248551 A1* | 10/2008 | Stinchcomb ........... A61K 47/42 435/236 |
| 2010/0324126 A1 | 12/2010 | Ihnat |
| 2011/0129534 A1 | 6/2011 | Gu |
| 2016/0045618 A1 | 2/2016 | Benedict |

FOREIGN PATENT DOCUMENTS

| | | |
|---|---|---|
| WO | WO-2005/058368 A1 | 6/2005 |
| WO | WO2016/048556 A1 | 3/2016 |

OTHER PUBLICATIONS

Burgess, S. W. and Shaw, W. A., Preparation of Surfactant and Lipid Vectors for Delivery of Proteins and Genes to Tissue, Acute Respiratory Distress Syndrome: Cellular and Molecular Mechanisms and Clinical Management, Plenum Press:125-131 (1998).
Draper, S. J. and Heeney, J. Viruses as vaccine vectors for infectious diseases and cancer, Nature Reviews Microbiology, 8: 62-73 (2010).
Samiey, B. et al., Effects of Surfactants on the Rate of Chemical Reactions, Hindawi Publishing Corporation Journal of Chemistry, 2014(Article ID908476):1-14 (2014).
Croyle, Ma, "Development of forumulations that enhance physical stability of viral vectors . . . " Gene Therapy, 2001, vol. 8, p. 1281-1290.
Nagabhushan, T.L., "Enhancement of intravesical delivery with Syn3 potentiates interferon . . . " Science Direct, 2007, vol. 18, p. 389-394.
Rosser, Charles J., "Gene therapy for superficial bladder cancer", Expert Review of Anticancer Therapy, 2001, vol. 1, Issue 4, p. 531-539.
Yamashita, Motoyuki, "Syn3 provides high levels of intravesical adenoviral-mediated gene transfer . . . " Cancer Gene Therapy, 2002, vol. 9, p. 687-691.
Dinney, C. P. N. et al., Phase I Trial of Intravesical Recobinant Adenovirus-Mediated Interferon-a2b Formulated in Syn3 for BCG failures in Non-Muscle-Invasive Bladder Cancer, J. Ural., 190(3):850-856 (2013).
Drexler, M. et al., What You Need to Know About Infectious Disease, Washington (DC): National Academies Press (US) (2010).
International Search Report for PCT/US2017/025728, 2 pages (dated Apr. 9, 2018).
NCI Thesaurus, "Nadofaragene Firadenovec" found at https://ncit.nci.nih.gov/ncitbrowser/ConceptReport.jsp?dictionary=NCI_Thesaurus&code=C104743 (Year: 2020).
Wiggan, O. et al., Novel formulations enhance the thermal stability of live-attenuated flavivirus vaccines, Vaccine, 29(43): 7456-7462 (2011).
Written Opinion for PCT/US2017/025728, 4 pages (dated Apr. 9, 2018).

* cited by examiner

*Primary Examiner* — M Franco G Salvoza
(74) *Attorney, Agent, or Firm* — Choate, Hall & Stewart LLP; Rolando Medina; Michael R. Hinrichsen

(57) ABSTRACT

Combining viral vector with surfactant preserves vector infectivity, and surfactant provided an unexpected benefit by protecting viral vector from damage due to transient elevated temperature.

20 Claims, No Drawings

VIRAL VECTOR STABILIZATION

RELATED APPLICATIONS

This application is a divisional of U.S. Ser. No. 15/781,707 filed 6 Jun. 2018, which is a United States National Stage entry of and asserts priority to PCT/US2017/025727 filed 3 Apr. 2017, which in turn asserts priority from United States provisional patent filing Ser. No. 62/322,452, filed 14 Apr. 2016, the contents of which are here incorporated by reference.

STATEMENT REGARDING FEDERALLY-SPONSORED RESEARCH OR DEVELOPMENT: NONE

NAMES OF THE PARTIES TO A JOINT RESEARCH AGREEMENT: NOT APPLICABLE

SEQUENCE LISTING: NONE

PRIOR DISCLOSURES BY AN INVENTOR: NONE

BACKGROUND

Infective viral particles are useful for many medical uses. For example, attenuated virus are useful as vaccines. Similarly, infective (yet often replication deficient) virus are useful as gene therapy vectors to deliver therapeutic transgenes.

The art teaches that infective virus particles are less than perfectly efficient in transfecting host cells. The art teaches that transfection efficiency may be increased by pre-treating the host cells with surfactant.

The art, however, also cautions that surfactant may damage viral particles, and thus reduce their infectivity. The art thus teaches to pre-treat host cells with surfactant immediately before viral vector transfection, yet avoid mixing the viral vector and surfactant and storing for any significant time. The art thus teaches to provide vector and surfactant as physically separate components for therapy.

We thus attempted to quantify the deleterious effect of surfactant on viral vector. To do so, we prepared a viral vector, measured its infectivity, mixed samples of it with surfactant, and stored the preparations under normal vector storage conditions and, to accelerate the deleterious effect of surfactant, at cycled elevated/cooled temperature (a common drug stability technique called "accelerated" stability testing).

BRIEF SUMMARY

We found that, directly contrary to our own expectations and the teachings of the art, surfactant does not reduce vector infectivity. To the contrary, we found that surfactant preserves vector infectivity: vector mixed with surfactant after storage showed higher infectivity than vector not mixed with surfactant. Further, surfactant provided a qualitatively-unexpected benefit, protecting viral vector from damage due to transient elevated temperature.

Our discovery thus for the first time opens the door to several advances in medical treatments. First, we have found a way to protect virus against heat damage by protecting the virus with surfactant. This enables therapeutic virus (e.g., vaccines or gene therapy vectors) to be manufactured, shipped, stored and distributed at higher temperatures than previously thought possible. This lessens the expense of distribution and increases the scope of the area where the virus may be safely distributed to physicians and patients.

Second, our discovery enables virus manufacturers to increase the shelf life of viral treatments. This enables manufacturers to manufacture in larger batch sizes, and may reduce the amount of virus-based medicines which must be discarded as being out-of-date.

BRIEF DESCRIPTION OF THE FIGURES: NONE

DETAILED DESCRIPTION

We tested the effect of surfactant on virus infectivity and surprisingly found that storage of a virus with surfactant does not in fact impair virus infectivity. To the contrary, our results show surfactant preserves it. This may be seen by our results in several experimental Examples.

Our Examples use The rAd-IFN virus. The rAd-IFN virus is a non-replicating recombinant adenovirus type 5 (Ad5)-based, interferon alpha-2b (IFNα2b) gene transfer vector. It is being developed as e.g., an intravesical treatment for superficial bladder cancer. rAd-IFN is used to deliver the human IFNα2b gene into cells in the urothelial lining of the bladder. The art teaches that on administration, Syn3™ excipient is included in the Admixture formulation immediately before administration to enhance gene transfer into bladder epithelium. We refer to "Admixture" as the final formulation of rAd-IFN in a patient finished dosage form; it contains rAd-IFN vector, Syn3™ and final formulation buffer ("FFB").

Our discussion of these Examples use the following abbreviations:

Admixture A mixture of rAd-IFN and Syn3™ and FFB representing the patient dose in Phase III clinical trial of the gene therapy product DP Drug Product DS Drug Substance FFB Final Formulation Buffer, i.e., a sterile buffer suitable for injection IFNα2b interferon alpha-2b rAd-IFN A replication deficient recombinant adenovirus type 5 based interferon alpha-2b gene transfer vector RT Room temperature, ~20 C.

Syn3™ SYN 3™ is the polyamide surfactant commercially available from the Schering-Plought Inc. division of Merck & Co. (Rahway, N.J.) and having the structure shown:

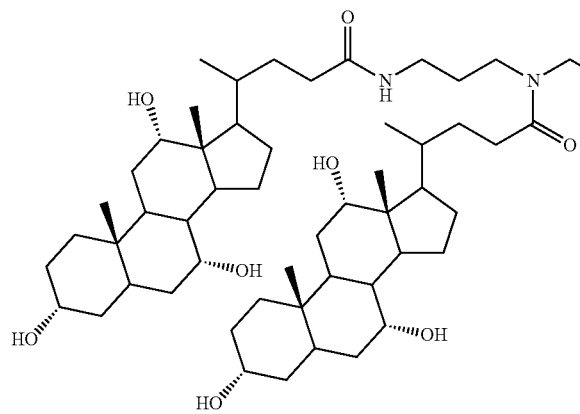
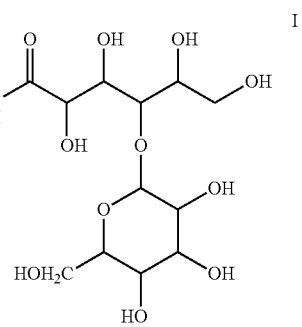

The art also uses the abbreviation "SYN3" to refer to the synapsin-3 protein, a protein involved in synaptic neurotransmission. We here use the term to refer to the synthetic surfactant, not the naturally-expressed neurotransmitter polypeptide.
TS Test sample Example 15-0029

The aim of this study was to assess the effect of Syn3™ DP on potency of the rAd-IFN gene therapy product in rAd-IFN potency assay. At the same time, two storage temperatures (RT and 2-8° C.) of Syn3™ DP powder were compared.

We used two samples of Syn3™, one stored in RT and one at 2-8° C. This study entailed performing of two rAd-IFN potency assays, each has one TS made from admixture, and a reference standard rAd-IFN from a known quantified batch as a control sample. One assay has the admixture with RT stored Syn3™ DP, the other admixture with Syn3™ DP stored in the fridge. The potency assay was conducted as known in the art.

We prepared two admixtures made from these samples, and compared them to each other and to reference standard material in a potency assay. Admixture containing $3\times10^{11}$ vp/ml of rAd-IFN was made and analyzed in a standard rAd-IFN potency assay. Two assays were run, both having ARKz001 as a control sample/reference standard.
Materials and Methods:
  We Prepared the Admixture as Follows:
  a) Add 20 ml of sterile water using a 20 ml syringe and 21G needle to one vial of Syn3™ DP sterile powder and gently agitate vial to mix for a couple of minutes. Allow contents to dissolve and bubbles to disappear for 40 minutes at ambient temperature and light. After reconstitution Syn3™ DP should be stored at room temperature and must be used within 24 hours. In this study, potency assay is started immediately after sample preparation.
  b) Take a vial of rAd-IFN DP (noting the batch number) from ultra-low temperature freezer (−70 C) and thaw at ambient temperature and light with periodic gentle agitation to mix contents while thawing. Once thawed, invert each vial several times to ensure contents are thoroughly mixed.
  c) Pipette 2.1 ml of FFB into a 15 ml tube.
  d) Withdraw dissolved Syn3™ DP using a 10 ml syringe and 21 G needle into a separate container. Pipette 1.4 ml of Syn3™ DP to the tube with FFB and invert several times to mix contents.
  e) Withdraw the rAd-IFN DP from the vial using 10 ml syringe and a longer 21 G needle. Use a separate container for the virus and pipette 5.3 ml to the admixture tube.
  f) Mix well by inverting admixture container several times.
  g) Final vp/ml concentration was $3\times1011$ vp/ml and volume was 8.8 ml.

We then performed the rAd-IFN potency assay. The prepared Admixture (from above) was used as a test sample. To continue to virus dilutions in potency assay, the admixture was diluted 1:6 in GM (1 ml of admixture+5 ml of GM; $5\times1010$ vp/ml), and then used as normal TS in potency assay. The reference standard material (ARKz001) is treated normally as in a standard procedure. To properly censor the resulting data, before the tests were run, we decided that in case the assays did not have enough passed plates/TS, the results would be given for information only.

Results from these first two analyses are summarized in the following Table. The rAd-IFN in admixture has average relative potency of 1.29 U/vp. Average potency value for rAd-IFN from three assays is 1.28 U/vp.

| Potency results of admixtures with differently stored Syn3. | | | |
|---|---|---|---|
| Assay | Syn3 stored at | U/vp of admixture | U/vp of ARKz001 |
| POT-15-037 | RT | 1.24 | 1.06 |
| POT-15-038 | 2-8° C. | 1.34 | 0.94* |
|  | Average | 1.29 |  |

*Only one plate passed statistical testing, potency value here for information only.

Our results confirm that storage of Syn3™ surfactant at RT does not in fact adversely affect Syn3™ by reducing the Potency of admixture made with it; to the contrary, even after storage at RT, Syn3™ appears to produce acceptable Potency.

In this first Example, two admixtures containing rAd-IFN were used as test samples in two potency assays. The admixtures were prepared with Syn3™ powder stored at RT and in the refrigerator to see if the storage condition of the Syn3™ powder might change the potency of the final Admixture. Our data from these assays served as proof that admixture as sample matrix can in fact be analyzed in a standard Potency assay, i.e., that surfactant does not interfere with a Potency assay.

From these first results, our conclusion is that admixture is a suitable sample type for potency assay and that storage in RT or fridge (2-8° C.) are both suitable for Syn3™ powder as far as potency of the final admixture is concerned.

Example 15-0029-ADD1

An in-use stability study for Admixture has been done where stability of admixture in four different catheters up to 24 hours has been tested. Surplus admixture at time point zero was frozen as 128×500 µl in ultra-low freezer (below −60° C.). Set of samples handled with a vent-needle is chosen for this study.

Assays used to estimate the stability of stored admixture are infectivity, potency, HPLC, pH and particle size. Total viral particle amount has been analyzed with HPLC instead of $OD_{260}$.

ARKz001 was employed as the control/reference standard sample in both assays and its potency values were within typically seen values. In one potency test, ARKz001 only passed statistical equivalence testing with one plate, so the potency value here is reported for information only. Nevertheless, the potency values from all of the plates were within expected potency values for ARKz001.

The aim of this follow-up work is to provide a baseline measures for a study of stability of rAd-IFN in its "ready-to-use" clinical formulation (as "Admixture") with diluent (sterile injectable buffer) and surfactant (e.g., Syn3™) when the preparation is thawed and frozen several times over a period of time per Example 15-0035 below.

Sixty-four (64) 500 µl aliquots of vent-needle admixture (prepared for additional testing) will be reserved as test samples in this work. All aliquots are thawed at each time point and three or four vials are taken for analyses. (1 vial for HPLC, 1 vial for particle size, 1 vial for infective titer and potency, 1 vial for pH) All remaining vials are frozen again to below −60° C. All analyses should be done on the same day if possible. If repeat assays are needed, individual vials will be thawed as needed.

Control Samples: Half of the aliquots (64 pcs) as prepared earlier (vent needle, additional testing) are reserved as control samples. These samples are thawed only as needed for each assay, so they will have only one freeze-thaw cycle before analyzing.

Analytical Methods: The analyses in this and Example 15-0035 will be done as presented in this Table. The time point windows are in −AT1.

| Stability study set-up | | | | | |
|---|---|---|---|---|---|
| Time point | HPLC | Infective titre | Potency | Particle size | pH |
| 0 M | x | x | x | x | x |
| 3 M | x | x | x | x | NA |
| 6 M | x | x | x | x | NA |
| 9 M | x | x | x | x | NA |
| 12 M | x | x | x | x | x |

Thawing Test Samples: The procedure to thaw test samples will be as follows:

(1) At the first time point, take sixty-four (64) vials (test samples) of vent-needle admixture and put them into a separate storage container from the other 64 vials, which are reserved for control samples. Continue with steps a)-d).

(2) At other time points go straight to step a).

a) Take all remaining aliquots that are intended for test samples and thaw them at RT until they melt.
b) Take three aliquots and put them in the fridge until assays can be done (on the same day).
c) Put the rest of the vials back to the ultra-low freezer.
d) Mark down in −AT1 of this plan that the aliquots have been thawed and frozen. Keep the attachment together with sample submission form/ultra-low freezer content logbook for the samples.

Testing is continued up to a year, which means that the test samples will undergo up to four thaws during this study whereas control samples only one.

HPLC is done on the samples, with a concentration of admixture of approximately $3 \times 10^{11}$ vp/ml. Infectivity of admixture is determined with flow cytometry; test sample together with the control/reference standard sample are measured in the same assay. Particle size analysis is done according to the dynamic light scattering method. The pH is determined at the last time point, to see if repeated thawing and freezing has affected e.g. microbial growth in the vials.

The results from the assays done at each time point are collected at time=0, 3, 6, 9 and 12 months, along with assays running numbers. There is a window of ±two weeks for the analyses. This study is continued up to 12 months. The results of the assays are compared to time point zero and to the control/reference standard sample that is run at every time point but with less freeze-thaw cycles. The time point zero result should be identical for both the test samples and the control/reference standard sample.

Our results for time t=0 are as follows:

| Results for 15-0029-ADD1 | | | | | | | | | |
|---|---|---|---|---|---|---|---|---|---|
| Appearance | pH | Viral Particle concentration (O.D.260) | Viral Particle Concentration (HPLC) | % change from previous measure | Infectivity Assay | % change from previous measure | Potency | % change from previous measure | Particle Size |
| Opalescent colorless solution, no visible particles | 7.76 | $10^{12}$ vp/mL (for information only) | $3.72^{11}$ vp/mL | N/A | $3.73^{10}$ NASIU/mL | N/A | 1.13 U/vp (for information only) | N/A | 113 nm |

Time = 0

These data confirm that the samples at t = 0 have been properly prepared.

These data confirm that the samples at t=0 have been properly prepared.

Example 15-0035

The aim of this study is to provide in-use stability and biocompatibility data for rAd-IFN in Admixture. From the samples prepared in Example 15-0015 ADD1 (above), sixty-four (64) vials have been be reserved as control samples, which are only thawed as needed for assays upon each time point. The rest of the vials will undergo several sequential freeze-thaw steps as they are all thawed at each time point, the needed vials are removed for analysis and the rest are frozen back.

rAd-IFN is a replication deficient recombinant adenovirus type 5 (rAd5) based gene transfer vector containing human interferon alpha-2b (IFN) gene in expression cassette that replaces E1a, E1b and pIX regions at the 5' end of adenovirus genome. The vector has been developed for intravesical treatment of non-muscle invasive bladder cancer. It is currently heading towards Phase III clinical trial. Formerly the product was known by the code SCH 721015 but currently it is referred as rAd-IFN.

rAd-IFN vector is used to deliver the human IFNα2b gene into cells in the urothelial lining of the bladder. Before intravesical administration, Admixture is prepared containing appropriate dose of the rAd-IFN drug product in final formulation buffer (FFB) and 1 mg/ml Syn3™ excipient which is included in the Admixture formulation to enhance gene transfer into bladder epithelium. This plan describes in-use stability and biocompatibility study protocol for rAd-IFN in admixture by mimicking phase III clinical scenario. The Admixture containing $3 \times 10^{11}$ vp/ml (Dose level 2) is exposed various specified delivery components during admixture preparation followed by holding in IntraVia sterile bag, withdrawal into syringes with 1 hour incubation and catheter administration. The study will include sampling at three different time points with four different catheter types:

Zero time point=Preparation of Admixture into IntraVia sterile bag followed by withdrawal into syringe, and delivery via four different types of catheters.

Hold 8h/RT time point=Admixture preparation into IntraVia sterile bag and holding in the dark at room temperature (RT) for 8 hours followed by 1 hour incubation at RT and ambient light, withdrawal into syringes followed by 1 hour incubation at RT and ambient light and delivery via four different types of catheters.

Hold 24h/+4° C. time point=Admixture preparation into IntraVia sterile bag and holding at refrigerated conditions (2-8° C.) for 24 hours followed by 1 hour incubation at RT and ambient light, withdrawal into syringes followed by 1 hour incubation at RT and ambient light and delivery via four different types of catheters.

The stability and biocompatibility will be assessed using the following assays to characterize any changes in appearance, the physical and chemical characteristics, biological properties and virus particle concentration and particle size of rAd-IFN in Admixture:

pH (Ph.Eur. 2.2.3)
Appearance (USP chapter 790 and Ph.Eur. 2.2.1 visual method, and Ph:Eur,2.2.2 modification of method I)
Potency assay
Infectivity assay
HPLC
$OD_{260}$
Particle size The admixture components are:
rAd-IFN DP—rAd-IFN-150702, $4.86 \times 10^{11}$ vp/ml, stored at Ultra low freezer
Syn3™ DP—Lyophilised powder lot 14071, stored at 2-8° C.
rAD-IFN FFB-rAd-IFN Diluent buffer lot FVTc001, stored at 2-8° C.
Aqua ad Iniectabilia Schedule for the in-use stability and biocompatibility study is presented in Table II. The prepared Admixture will be divided equally into two 60 ml syringes and will be used for administration of two different catheters. Both catheters are operated at same time by two separate operators. There are no hold step for zero time point, transfer via catheters and sampling will be performed immediately after admixture preparation followed by sample analysis. For the Hold 8 h/RT time point, prepared Admixture in IntraVia bag will be stored in the dark for 8 hours at RT. For the Hold 24 h/+4° C. time point, prepared Admixture in IntraVia bag will be stored for 24 hours at fridge. Both hold time points also include 1 hour incubation in IntraVia bag at RT and ambient light before withdrawal into 60 ml syringes and 1 hour incubation at RT and ambient light in syringes.

TABLE II

Schedule for the in-use stability and biocompatibility study

| | Week −2 Day 1 | Week −2 Day 2 | Week 1 Day 1 | Week 1 Day 2 | Week 2 Day 1 | Week 2 Day 2 |
|---|---|---|---|---|---|---|
| Zero time point | Admixture preparation, Cat1 and Cat2 sampling and analysis | | Admixture preparation, Cat3 and Cat4 sampling and analysis | | | |
| Hold 8 h/RT time point | | | | | Admixture preparation, Cat1 and Cat2 sampling and analysis | Admixture preparation, Cat3 and Cat4 sampling and analysis |
| Hold 24 h/+4° C. time point | Admixture preparation | Cat1 and Cat2 sampling and analysis | Admixture preparation, | Cat3 and Cat4 sampling and analysis | | |

Preparation of Admixture:

The Admixture containing $3 \times 10^{11}$ vp/ml (Dose level 2) may be prepared under laminar flow hood as follows:

1. To obtain a Syn3™ solution, add sterile water using a syringe and needle to a vial of Syn3™ powder and gently agitate vial to mix. Allow contents to dissolve. After reconstitution Syn3™ should be used within 24 hours.

2. Remove vials of rAd-IFN from the freezer and thaw with periodic gentle agitation. Once thawed, invert each vial several times to ensure contents are thoroughly mixed.
3. Add Dilution buffer into an empty mixing vessel.
4. Withdraw dissolved Syn3™ solution and introduce into mixing vessel containing the Dilution buffer. Invert the vessel several times to mix contents well.
5. Add rAd-IFN to the mixing vessel and mix gently.

We intend to use the following Analytical assays:

Biological activity of rAd-IFN will be assessed by determining potency and infectivity in suitable cell lines. Appearance will be determined and physical and chemical properties will be characterized by measuring pH. Viral particle concentration and size will be determined using high performance liquid chromatography (HPLC), absorbance at 260 nm (OD260) and particle size assays. All methods are qualified/assay qualification is on-going 81 for this product.

After the completion of the single assay the accepted result will be transferred to a result collection form or laboratory notebook which will contain all the results and assay references for this stability study.

Potency: The potency assay models all steps of the therapeutic mechanism of rAD-IFN: infection of cells, expression of IFN and antitumor activity of the product and measures the killing efficacy of rAd-IFN. Interferon sensitive human bladder cancer cells are transduced using multiple dilutions of reference standard and test samples leading to expression of IFNα2b and subsequent cell death. Interferon-sensitive cells may be purchased commercially from several sources, or may be readily prepared or isolated as is well known in the art. See e.g., Howard R. Hubbell et al., *Independent sensitivity of Human Tumor Cell Lines To Interferon and Double-Stranded RNA*, 44 Cancer Res., 3252 (1984); Lawrence M. Pfeffer et al., *Cytoskeletal Association of Human a-Interferon Receptor Complexes In Interferon-Sensitive and -Resistant Lymphoblastoid Cells*, 84 P.N.A.S. 3249, 3249 col. 1 (1987). Cell killing efficiency is determined using a colorimetric method measuring dehydrogenase activity of the living cells. The relative potency of the test sample is determined against the reference standard response curve after testing parallelism by equivalence test as outlined in Ph. Eur. 5.3 and USP <1034>. The assay may be performed as described in *Viral Vector Assay and Vector*, U.S. Patent Application Ser. No. 62/218,810 filed 15 Sep. 2015, incorporated here by reference.

Infectivity: In infectivity assay, cells that support adenovirus replication are infected with different concentrations of adenovirus. After infection, percentage of infected cells is determined with a flow cytometer utilizing a fluorescently conjugated antibody against an adenoviral structural protein. Samples are analysed in parallel with a reference standard and infectivity is given as relative Infectious Units/ml. Result is calculated using Slope Ratio method as outlined in Ph. Eur. 5.3 and USP <1034> The assay may be performed as described in *Viral Vector Assay and Vector*, U.S. Patent Application Ser. No. 62/218,810 filed 15 Sep. 2015.

pH: pH of rAd-IFN drug products is buffered around pH 7.8 to ensure acceptability for instillation and long term maintenance of the adenovirus function. The desired pH is confirmed by measuring the sample in solution using a standardized pH meter at room temperature. Test is done according to Ph. Eur. 2.2.3 and USP <38>.

Appearance: Appearance (clarity and degree of opalescence, degree of coloration and determination of visible particulates) of adenoviral vector samples is determined according to European Pharmacopoeia (EP) using visual method (EP 2.2.1 visual method and EP 2.2.2 modification of method I) harmonized with United States Pharmacopoeia (USP) chapter 790 guidelines. The assay may be performed as described in *Viral Vector Assay and Vector*, U.S. Patent Application Ser. No. 62/218,810 filed 15 Sep. 2015.

HPC: HPLC is used to determine total viral particle of rAd-IFN. Working standard (WS) is used to establish a standard curve. The obtained peak areas are plotted against known virus particle concentration of WS (vp/ml). Virus particle concentration of test samples is interpolated from the standard curve and multiplied with dilution factor. Test samples are analysed as duplicates, and results are reported as average result of two replicate samples. The assay may be performed as described in *Viral Vector Assay and Vector*, U.S. Patent Application Ser. No. 62/218,810 filed 15 Sep. 2015.

$OD_{260}$: Total viral particle concentration of a drug product must reflect the safe and efficacious dose. The concentration of rAd-IFN is determined spectrophotometrically by measuring optical density at 260 nm ($OD_{260}$) in presence of 0.1% SDS. SDS is used to lyse the viral capsid. A conversion factor of $1.1 \times 10^{12}$ particles per absorbance unit at 260 nm is used. This value is based on scientific literature as well as internal findings. Negative control is used to determine background absorbance to be substracted from the results and positive control to confirm the assay performance.

Particle size: Particle size assay is used to monitor possible particle aggregation. The assay is based on dynamic light scattering, where a laser beam is directed to the analyzed sample and the intensity of scattered light is measured from specific detection angle. The smaller the size of soluble particles, the faster the particles movement in the surrounding liquid and the faster the intensity changes of scattered light. Particle size can be calculated based on data obtained from the fluctuations in the light intensity versus time profile. Particle size assay for rAd-IFN may be performed as known in the art.

SUMMARY

Given our examples, one can derive from them a number of therapeutically valuable and commercially valuable applications. These include, for example:

1. A composition of matter comprising an infective virus in a therapeutically-effective amount and lyophilized to remove substantially all water, mixed with a surfactant in an amount effective to preserve the infectivity of the virus.
2. The composition of matter of paragraph 1, wherein the surfactant is in an amount effective to preserve the infectivity of the virus during storage at elevated temperature.
3. The composition of matter of paragraph 1, wherein the surfactant comprises Syn3™.
4. The composition of matter of matter of paragraph 1, wherein the infective virus functions as a therapeutic vaccine.
5. The composition of matter of paragraph 1, wherein the infective virus functions as a gene therapy vector.

Given our examples, the artisan may readily devise further variants and modifications on our general theme. For example, while our actual experimental examples involve Syn3™ other surfactants are known in the art as useful for increasing viral transfection efficiency. Functionally equivalent surfactants are described, for example, in William BENEDICT, *Methods and Compositions for Treatment of Interferon Resistant Tumors*, WO 2005/058368 (30 Jun. 2005) at [0054]-[0055].

Similarly, while our actual experiments used replication-deficient virus, we expect our invention would provide the same benefit to replication-competent virus. Similarly, while our actual experiments used adenovirus, we expect our invention would provide similar benefits to other infective virus preparations using other genera of virus (e.g., adeno-associated virus) and other specific viruses (e.g., measles, mumps and rubella attenuated live virus, oral polio, etc.). Indeed, we expect our invention to also be useful for attenuated bacterial vaccines which use bacterium which are live yet inactive (e.g., *Rickettsia* sp., *Salmonella typhi* and *Bacillus* Calmette-Guerin vaccines).

Similarly, certain of our claims require "transient" storage at elevated temperature. We intend this term to cover periods longer than that known in the art to not adversely affect virus vector infectivity, but not permanent or long-term storage; longer than half an hour perhaps, but shorter than a week. We thus intend the coverage of our patent to be defined not by our specific examples discussed here, but by the legal claims and permissible legal equivalents of them.

The invention claimed is:

1. A lyophilized composition comprising an infective recombinant adenovirus mixed with a surfactant in an amount effective to preserve the infectivity of the recombinant adenovirus, wherein the composition contains substantially no water, wherein the recombinant adenovirus comprises a transgene, and wherein the surfactant has Structure I:

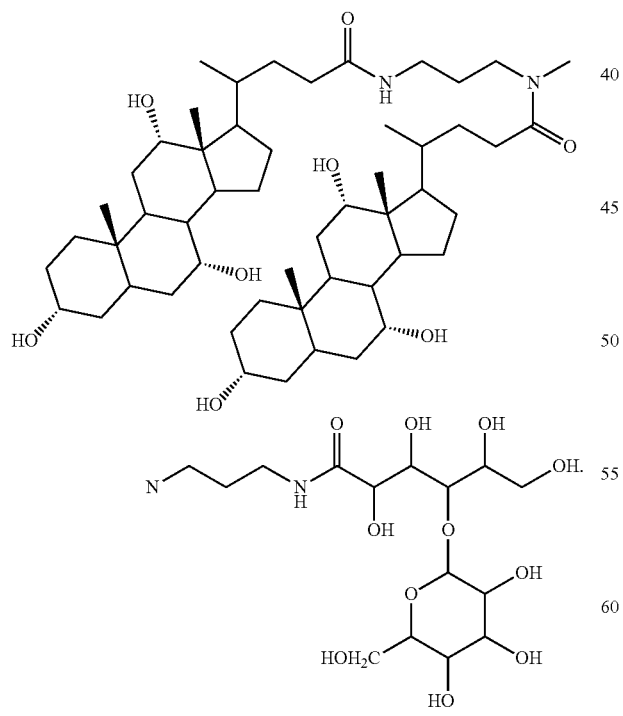

2. The composition of claim 1, wherein the recombinant adenovirus is replication-deficient.

3. The composition of claim 1, wherein the surfactant is in an amount effective to preserve the infectivity of the recombinant adenovirus at a temperature of at least about 2° C.

4. The composition of claim 3, wherein the surfactant is in an amount effective to preserve the infectivity of the recombinant adenovirus during transient storage at a temperature of at least about 2° C.

5. The composition of claim 1, wherein the recombinant adenovirus functions as a therapeutic vaccine.

6. The composition of claim 1, wherein the recombinant adenovirus functions as a gene therapy vector.

7. The composition of claim 1, wherein the composition comprises a therapeutically-effective amount of the recombinant adenovirus.

8. A lyophilized composition comprising an infective recombinant adenovirus and a surfactant, the surfactant in an amount effective to preserve the infectivity of the recombinant adenovirus agent, whereby (a) the infectivity of the recombinant adenovirus combined with the surfactant is at least 100% of (b) the infectivity of the recombinant adenovirus without the surfactant when stored under the same conditions and for the same time, wherein the composition contains substantially no water, and wherein the surfactant has Structure I:

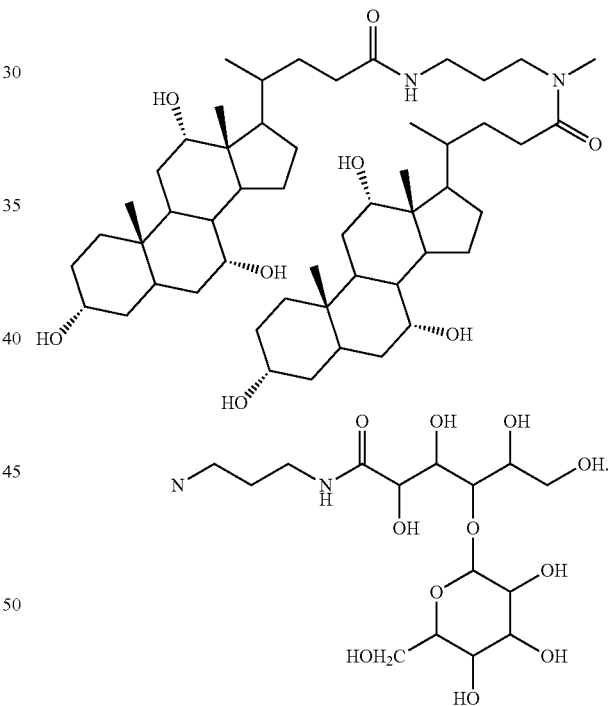

9. The composition of claim 8, wherein (a) the infectivity of the recombinant adenovirus combined with the surfactant is at least 117% of (b) the infectivity of the recombinant adenovirus without the surfactant when stored under the same conditions and for the same time.

10. The composition of claim 9, wherein (a) the infectivity of the recombinant adenovirus combined with the surfactant is at least 129% of (b) the infectivity of the recombinant adenovirus without the surfactant when stored under the same conditions and for the same time.

11. The composition of claim 10, wherein (a) the infectivity of the recombinant adenovirus combined with the surfactant is at least 142% of (b) the infectivity of the recombinant adenovirus without the surfactant when stored under the same conditions and for the same time.

12. The composition of claim 8, whereby (a) the infectivity of the recombinant adenovirus combined with the surfactant is at least 100% of (b) the infectivity of the recombinant adenovirus without the surfactant when stored under the same conditions for at least three months.

13. The composition of claim 12, whereby (a) the infectivity of the recombinant adenovirus combined with the surfactant is at least 100% of (b) the infectivity of the recombinant adenovirus without the surfactant when stored under the same conditions for twelve months.

14. The composition of claim 8, whereby (a) the infectivity of the recombinant adenovirus combined with the surfactant is at least 100% of (b) the infectivity of the recombinant adenovirus without the surfactant when stored under the same conditions and for the same time, wherein the conditions comprise at least one freeze-thaw cycle.

15. The composition of claim 8, wherein the recombinant adenovirus is replication-deficient.

16. The composition of claim 8, wherein the surfactant is in an amount effective to preserve the infectivity of the recombinant adenovirus at a temperature of 2° C.

17. The composition of claim 8, wherein the recombinant adenovirus functions as a therapeutic vaccine.

18. The composition of claim 8, wherein the recombinant adenovirus functions as a gene therapy vector.

19. The composition of claim 18, wherein the recombinant adenovirus is a replication-deficient adenovirus and cannot replicate in normal human cells.

20. The composition of claim 19, wherein the replication-deficient adenovirus comprises nadofaragene firadenovec.

\* \* \* \* \*